(12) United States Patent
Groat et al.

(10) Patent No.: US 7,776,546 B2
(45) Date of Patent: Aug. 17, 2010

(54) METHOD AND DEVICE FOR DETECTING FELINE IMMUNODEFICIENCY VIRUS

(75) Inventors: Randall G. Groat, Freeport, ME (US); Quentin J. Tonelli, Portland, ME (US)

(73) Assignee: IDEXX Laboratories, Inc., Westbrook, ME (US)

( * ) Notice: Subject to any disclaimer, the term of this patent is extended or adjusted under 35 U.S.C. 154(b) by 390 days.

(21) Appl. No.: 10/938,097

(22) Filed: Sep. 10, 2004

(65) Prior Publication Data

US 2005/0058993 A1 Mar. 17, 2005

Related U.S. Application Data

(60) Provisional application No. 60/584,106, filed on Jun. 30, 2004, provisional application No. 60/501,982, filed on Sep. 11, 2003.

(51) Int. Cl.
*C12Q 1/70* (2006.01)
*G01N 33/53* (2006.01)

(52) U.S. Cl. .......................... 435/7.1; 435/5; 435/7.72; 435/7.9

(58) Field of Classification Search .................. 435/4, 435/7.1; 424/184.1, 185.1, 186.1, 187.1, 424/188.1
See application file for complete search history.

(56) References Cited

U.S. PATENT DOCUMENTS

| | | | |
|---|---|---|---|
| 4,629,783 A | 12/1986 | Cosand | |
| 4,879,212 A | 11/1989 | Wang et al. | |
| 4,900,548 A | 2/1990 | Kitchen | |
| 5,037,753 A | 8/1991 | Pedersen et al. | |
| 5,118,602 A | 6/1992 | Pedersen et al. | |
| 5,177,014 A | 1/1993 | O'Connor et al. | |
| 5,219,725 A | 6/1993 | O'Connor et al. | |
| 5,565,319 A | 10/1996 | Pedersen et al. | |
| 5,576,177 A | 11/1996 | Fridland et al. | |
| 5,591,572 A | 1/1997 | Kemp et al. | |
| 5,627,026 A | 5/1997 | O'Connor et al. | |
| 5,648,209 A | 7/1997 | Avrameas et al. | |
| 5,656,732 A | 8/1997 | Andersen et al. | |
| 5,705,331 A | 1/1998 | Arthur et al. | |
| 5,726,013 A | 3/1998 | Clark | |
| 5,736,378 A | 4/1998 | Elder et al. | |
| 5,750,333 A | 5/1998 | Clark | |
| 5,820,869 A | 10/1998 | Wasmoen et al. | |
| 5,833,993 A | 11/1998 | Wardley | |
| 5,846,825 A | 12/1998 | Yamamoto | |
| 5,849,303 A | 12/1998 | Wasmoen et al. | |
| 5,994,516 A | 11/1999 | Pancino et al. | |
| 6,077,662 A | 6/2000 | Compans et al. | |
| 6,228,608 B1 | 5/2001 | Young et al. | |
| 6,254,872 B1 | 7/2001 | Yamamoto | |
| 6,284,253 B1 | 9/2001 | Barr et al. | |
| 6,300,118 B1 | 10/2001 | Chavez et al. | |
| 6,331,616 B1 | 12/2001 | Tompkins et al. | |
| 6,383,765 B1 | 5/2002 | Andersen et al. | |
| 6,391,304 B1 | 5/2002 | Richardson et al. | |
| 6,447,993 B1 | 9/2002 | Yamamoto | |
| 6,455,265 B1 | 9/2002 | Serres | |
| 6,458,528 B1 | 10/2002 | Groat et al. | |
| 6,503,713 B1 | 1/2003 | Rana | |
| 6,613,530 B1 | 9/2003 | Wienhues et al. | |

FOREIGN PATENT DOCUMENTS

| | | |
|---|---|---|
| EP | 0 602 406 B1 | 11/1997 |
| EP | 0 887 412 A1 | 12/1998 |
| EP | 0 962 774 A1 | 12/1999 |
| EP | 0577 458 B1 | 9/2004 |
| JP | 02-11524 A | 1/1990 |
| JP | 07-159408 A | 6/1995 |
| WO | WO 90/06510 | 6/1990 |
| WO | WO/90/13573 | 11/1990 |
| WO | WO 92/09632 | 6/1992 |
| WO | WO 92/22573 | 12/1992 |
| WO | WO 93/01304 | 1/1993 |
| WO | WO 94/02612 | 2/1994 |
| WO | WO 94/06471 | 3/1994 |
| WO | WO 96/40268 | 12/1996 |

(Continued)

OTHER PUBLICATIONS

Rimmelzwaan et al. gag- and env-specific serum antibodies in cats after natural and experimental infection with feline immunodeficiency virus. Veterinary Microbiology, Mar. 1994, vol. 39, Issues 1-2, p. 153-165.*

(Continued)

*Primary Examiner*—Robert B Mondesi
*Assistant Examiner*—Louise Humphrey
(74) *Attorney, Agent, or Firm*—McDonnell Boehnen Hulbert & Berghoff LLP

(57) ABSTRACT

A method and device for determining a feline immunodeficiency virus infection or vaccination in an animal. The method includes contacting a biological sample from a felid with various FIV polypeptides and determining the binding of antibodies in the sample to the polypeptides. The determination of whether an animal is infected with FIV or has been vaccinated against FIV can be determined by measuring the animal's immune response to an FIV env polypeptide. A device for detecting FIV antibodies is provided.

15 Claims, No Drawings

FOREIGN PATENT DOCUMENTS

| WO | WO 96/40953 | 12/1996 |
|---|---|---|
| WO | WO 96/40956 | 12/1996 |
| WO | WO 96/40957 | 12/1996 |
| WO | WO 97/07817 | 3/1997 |
| WO | WO 99/29182 | 6/1999 |
| WO | WO 01/04280 | 1/2001 |
| WO | WO 03/015814 | 2/2003 |
| WO | WO 2004/100985 | 11/2004 |

OTHER PUBLICATIONS

Calzolari et al. Serological diagnosis of feline immunodeficiency virus infection using recombinant transmembrane glycoprotein. Veterinary Immunology and Immunopathology 1995, vol. 46, p. 83-92.*
Wimley et al. Designing Transmembrane R-Helices That Insert Spontaneously. Biochemistry 2000, vol. 39, p. 4432-4442.*
U.S. Appl. No. 10/938,056, filed Sep. 10, 2004, Groat, et al.
U.S. Appl. No. 11/015,675, filed Dec. 17, 2004, Groat, et al.
U.S. Appl. No. 11/059,285, filed Feb. 16, 2005, Groat, et al.
U.S. Appl. No. 11/076,820, filed Mar. 10, 2005, Groat, et al.
U.S. Appl. No. 11/077,321, filed Mar. 10, 2005, Groat, et al.
U.S. Appl. No. 11/075,480, filed Mar. 9, 2005, Groat, et al.
U.S. Appl. No. 11/075,958, filed Mar. 9, 2005, Groat, et al.
Olmsted, R.A. et al, "Molecular cloning of the feline immunodeficiency virus", Proc. Nat. Acad. Sci. USA, 1989, vol. 86, pp. 2448-2452.
Maki, N. et al., "Molecular Characterization and Heterogeneity of Feline Immunodeficiency Virus Isolates", Archives of Virolology, 1992, vol. 123, pp. 29-45.
Yamamoto, J.K. et al., "Experimental Vaccine Protection against Homologous and Heterologous Strains of Feline Immunodeficiency Virus", Journal of Virology, 1993, vol. 67, No. 1, pp. 601-605.
Hohdatsu, T. et al., "Effect of Dual-subtype Vaccine Against Feline Immunodeficiency Virus Infection", Veterinary Microbiology, 1997, vol. 58, pp. 155-165.
Uhl, E.W. et al., "FIV Vaccine Development and its Importance to Veterinary and Human Medicine; A Review FIV Vaccine 2002 Update and Review", Veterinary Immunology and Immunopathology, 2002, vol. 90, pp. 133-132.
Murray, D.M., "Identifying FIV Vaccinates", Journal of the American Veterinary Medical Association, 2003, vol. 222, p. 710.
Moon, D., "Another Solution to Identify FIV-Vaccinated Cats", Journal of the American Veterinary Medical Association, 2003, vol. 22, No. 9, p. 1207.
Calandrella, M., "Desitometric Analysis of Western Blot Assays for Feline Immunodeficiency Virus Antibodies", Veterinary Immunology and Immunopathology, 2001, vol. 79, pp. 261-271.
Hartmann, K. et al., "Comparison of Six In-House Tests for the Rapid Diagnosis of Feline Immunodeficiency and Feline Leukemia Virus Infections", The Veterinary Record, 2001, vol. 149, pp. 317-320.
Richardson, J., et al., "Delayed Infection after Immunization with a peptide from the Transmembrane Glycoprotein of the Feline Immunodeficiency Virus", Journal of Virology, 1998, vol. 72, pp. 2406-2415.
Finerty, Susan, et al., "Mucosal immunization with experimental feline immunodeficiency virus (FIV) vaccines induces both antibody and T cell responses but does not protect against rectal FIV challenge", Vaccine, 2000, vol. 18, pp. 3254-3265.
DeRonde, Anthony, et al., "Antibody Response in Cats to the Envelope Proteins of Feline Immunodeficincy Virus: identification of an Immunodominant Neutralization Domain", Virology, 1994, vol. 198, pp. 257-264.
Lombardi, Stefania, et al., "Identification of a Linear Neutralization Site within the Third Variable region of the Feline Immunodeficiency Virus Envelope", Journal of Virology, 1993, vol. 67, pp. 4742-4749.
Avrameas, A., et al., "Localisation of Three Epitopes of the ENV Protein of Feline Immunodeficiency Virus", Molecular Immunology, 1992, vol. 29, pp. 565-572.
Avrameas, A., et al., "Serological Diagnosis of Feline Immunodeficiency Virus Infection Based on Synthetic Peptides from Env Glycoproteins", Res. Virol, 1993, vol. 144, pp. 209-218.
Olmsted, Robert, "Nucleotide Sequence Analysis of Feline Immunodeficiency Virus: Genome Organization and Relationship to Other Lentiviruses", Proc. Natl. Acad. Sci. USA, 1989, vol. 86, pp. 8088-8092.
Gallaher, William, et al., "A General Model for the Transmembrane Proteins of HIV and Other Retroviruses", AIDS Research and Human Retroviruses, 1989, vol. 5, pp. 431-440.
Mermer, B., et al., "Similarities Between the Transmembrane Proteins of FIV and HIV", Abstract distributed on and Poster Presentation during the Cold Spring Harbor Conference, 1991.
Javaherian, et al., "Principal neutralizing domain of the human immunodeficiency virus type 1 envelope protein", Proc. Natl. Acad. Sci. USA, 1989, vol. 86, pp. 6768-6772.
Steinman, et al., "Biochemical and Immunological Characterization of the Major Structural Proteins of Feline Immunodeficiency Virus", Journal of General Virology, 1990, vol. 71, pp. 701-706.
Gnann, et al, "Fine Mapping of an Immunodominant Domain in the Transmembrane Glycoprotein of Human Immunodeficiency Virus", Journal of Virology, 1987, vol. 61, pp. 2639-2641.
Chong, et al., "Analysis of Equine Humoral Immune Responses to the Transmembrane Envelope Glycoprotein (gp45) of Equine Infectious Anemia Virus", Journal of Virology, 1991, pp. 1013-1018.
Berton, et al., "The Antigenic Structure of the Influenza B Virus Hemagglutinin: Operational and Topological Mapping with Monoclonal Antibodies", Virology, 1985, vol. 143, pp. 583-594.
Mermer, et al., "A Recombinant-based Feline Immunodeficiency Virus Antibody Enzyme-Linked Immunosorbent Assay", Veterinary Immunology and Immunopathology, 1992, vol. 35, pp. 133-141.
Massi, et al., "Most Potential Linear B Cell Epitopes of Env Glycoproteins of Feline Immunodeficiency Virus are Immunogenically Silent in Infected Cats", AIDS Research and Human Retroviruses, 1997, vol. 13, pp. 1121-1129.
Lutz, et al., "FIV Vaccine Studies I, Immune Response to Recombinant FIV ENV Gene Products and Outcome After Challenged Infection", Veterinary Immunology and Immunopathology, 1995, vol. 46, pp. 103-113.
Tijhaar, Edwin, et al., "Salmonella typhimurium AroA Recombinants and Immune-stimulating Complexes as Vaccine Candidates for Feline Immunodeficiency Virus", Journal of General Virology, 1997, vol. 78(12), pp. 3265-3275.
Fort Dodge Animal Health, First Feline Aids Vaccine Available, Press Release, Aug. 12, 2002.
Fel-O-Vax® FIV Product Brochure, 2002 Fort Dodge Animal Health.
Ponsati, Berta, et al., A Synthetic Strategy for Simulatenous Purification-Conjugation of Antigenic Peptides, Analytical Biochemistry, 181:389-395 (1989).
Pancino, et al., B Epitopes and Selection Pressures in Feline Immunodeficiency Virus Envelope Glycoproteins, Journal of Virology, 67(2):664-672 (1993).
Erdenbaatar, et al., Enzyme-Linked Immunosorbent Assay to Differentiate the Antibody Responses of Animals Infected with Brucella Species from Those of Animals Infected with Yersinia enterocolitica 09, Clinical and Diagnostic Laboratory Immunology, 10(4):710-714 (2003).

* cited by examiner

METHOD AND DEVICE FOR DETECTING FELINE IMMUNODEFICIENCY VIRUS

CROSS-REFERENCE TO RELATED APPLICATIONS

This application claims the benefit of U.S. Provisional Patent Application Ser. No. 60/584,106, filed Jun. 30, 2004, and U.S. Provisional Patent Application Ser. No. 60/501,982 filed Sep. 11, 2003.

FIELD OF THE INVENTION

The invention is related to the detection of antibodies directed to Feline Immunodeficiency Virus.

BACKGROUND OF THE INVENTION

Feline immunodeficiency virus (FIV), formerly called feline T-lymphotrophic lentivirus, was first isolated in 1986 from a large multiple cat household in Petaluma, Calif. (Pederson et al., Science (1987) 235:790). FIV infects cats to produce an AIDS-like syndrome. Although FIV is morphologically and pathologically similar to the human immunodeficiency virus (HIV), it has been shown to be antigenically distinct from HIV. Like HIV, once a cat becomes infected with FIV, the disease progresses from a primary infection (viraemia, fever, general lymphadenitis) to a lengthy asymptomatic phase, followed by severe impairment in immune function caused by a reduction in CD4 lymphocytes, and resulting in heightened susceptibility to secondary infections and ultimately death.

FIV has been classified as a member of the subfamily Lentiviridae in the family Retroviridae, the family that includes human and simian immunodeficiency viruses, equine infectious anaemia, maedi visna of sheep and caprinearthritis encephalitis viruses (CAEV). The genome of FIV is organized like other lentiviruses with three long open reading frames corresponding to gag, pol and env (Talbott et al., Proc. Natl. Acad. Sci. (1989) 86:5743; Olmsted et al., Proc. Natl. Acad. Sci. (1989) 86:2448). The gag gene codes for the major structural components of the virus, the env gene codes for the envelope glycoprotein, and the pol gene codes for the polymerase protein.

The gag gene is expressed as a 55 kD polyprotein that is processed into three subunits: a p15 matrix protein, a p24 capsid protein, and a p10 nucleocapsid protein. The pol gene encodes three proteins: the protease, reverse transcriptase and a p14.6 protein of unknown function. Autoprocessing by the protease portion of the gene gives rise to all three proteins of the pol region. Additionally, the protease is responsible for the processing of the gag precursor. The pol gene is expressed as a gag-pol fusion protein. The envelope gene is expressed as a 160 kD glycoprotein, gp 160. The antigenicity of the FIV core proteins is similar to other lentiviruses.

Several independent viral isolates have been prepared across the world, and a certain number of studies have been carried out in order to demonstrate the structure of the isolated strains: the American strain Petaluma, Talbott et al. Natl. Acad. Sci. USA, 1989, 86, 5743-5747; Philipps et al., J. Virol., 1990, 64, 10, 4605-4613), the Japanese strains (the TM1 and TM2 strains), Miyazawa et al., Arch. Virol., 1989, 108, 59-68, and the Swiss isolates (FIVZ1 and FIVZ2), Morikawa et al., Virus Research, 1991, 21, 53-63.

The nucleotide sequences of three proviral clones derived from American FIV isolates (Petaluma strain) have been described (clones FIV34TF10, FIV14 and isolate PPR) (Olmsted, et al. 1989; Philipps et al., 1990; Talbott et al., 1989) and compared with two Swiss isolates (Morikawa et al. 1991). This comparison led Morikawa et al. to specify the presence of certain conserved regions and certain variable regions within the env gene of FIV. French strains have also been isolated (strains Wo and Me)(Moraillon et al., 1992, Vet. Mic., 31, 41-45).

The virus replicates optimally in blood mononuclear cells and has a tropism for T-lymphocytes, peritoneal macrophage, brain macrophage and astrocytes. In common with other retroviruses, the genetic material of FIV is composed of RNA and the production of a DNA copy of the viral RNA is an essential step in the replication of FIV in the host. This step requires the enzyme reverse transcriptase that is carried into the host by the invading virus. The DNA version of the viral genome is inserted into the genetic material of infected host cells in which it continues to reside as a provirus. This provirus is replicated every time the cell divides and can code for the production of new virus particles. Cells infected with FIV remain infected for the duration of their lifespan.

The virus appears to be spread naturally by horizontal transmission, predominantly by bite wounds from an infected cat as these animals shed appreciable amounts of virus in saliva (Yamamoto et al., Am. J. Vet. Res. 1988, 8:1246). Vertical transmission has been reported, but is rare.

Current diagnostic screening tests for FIV infection detect serum antibody (Ab) to FIV. Virus detection kits are also available but not as prevalent. A number of diagnostic tests are available to determine the presence of FIV antibody in infected animals. For example, PETCHEK® FIV Ab test kit and the SNAP® Combo FeLV Ag/FIV Ab test kit (IDEXX Laboratories, Westbrook, Maine) are immunoassay based diagnostic tests for FIV infection.

Detecting FIV infection is becoming increasingly important as studies reveal FIV infection is widespread worldwide. As vaccines have been developed in attempt to combat the disease, it is even more important to be able to detect the effectiveness of a vaccine and to discriminate between vaccinated cats versus naturally infected cats.

SUMMARY OF THE INVENTION

In one aspect, the present invention provides a method for determining whether a felid has been vaccinated against FIV or is naturally infected with FIV by determining the felid's immune response to an FIV polypeptide, such as an FIV env polypeptide.

In another aspect, the invention is directed to a method of distinguishing among animals that have been naturally infected with FIV versus animals that have not been infected or have been vaccinated against an FIV infection. The method includes contacting a biological sample from an animal with a polypeptide that does not substantially bind to an FIV antibody that is a significant component of the animal's immune response to an FIV vaccine. FIV antibodies in the sample that substantially bind to the polypeptide are detected. It is determined that the animal is naturally infected by correlating a positive result in the detecting step to a natural infection and it is determined that the animal has been vaccinated or not infected by correlating a negative result to a vaccination or no infection. The polypeptide may be derived from FIV env.

In a further aspect, the invention is directed to a method of determining whether a cat has been vaccinated against FIV or is naturally infected with FIV. The method includes (a) detecting, before a period a time following vaccination sufficient for certain FIV antigen-specific antibodies raised in response to the vaccine to be not detected, whether the cat has antibodies against an FIV peptide; (b) detecting, after a period of time following vaccination sufficient for certain FIV antigen-specific antibodies raised in response to the vaccine to be not detected, whether the cat has antibodies against an FIV polypeptide; (c) determining that the animal has been vaccinated by detecting antibodies in step a but not in step b, and (d) determining that the animal is naturally infected by detecting antibodies in steps a and b.

The invention also provides for a method of determining whether a cat has not been infected by FIV or has been vaccinated against FIV. The method includes analyzing a biological sample from the cat to detect antibodies against a polypeptide derived from FIV, and determining that the animal has not been infected or has been or vaccinated by not detecting such antibodies.

In yet another aspect, the invention provides a method of determining whether or not a cat has been vaccinated for FIV or naturally infected with FIV. The method includes providing a test device comprising a polypeptide, obtaining a blood sample from a cat, running the blood sample on the test device, and reading the test device. A positive result indicates the cat has been naturally infected with FIV or vaccinated against FIV and a negative result indicates the cat has not been naturally infected with FIV and not vaccinated against FIV.

Still further, the invention is directed to a diagnostic device having a dry porous carrier, a first detection reagent immobilized on the porous carrier where the first detection reagent includes a protein that captures FIV antibodies generated by a host in response to either a natural FIV infection or an FIV vaccination, and a second detection reagent immobilized on the porous carrier wherein the second detection reagent includes a protein that captures FIV antibodies generated by a host in response to a natural FIV infection but does not substantially capture antibodies generated by the host in response to an FIV vaccination. The first detection reagent may be FIV p15 or p24 antigen, and the second detection reagent may be an FIV env protein.

In another aspect, the invention is directed to novel FIV polypeptides.

DETAILED DESCRIPTION

Before describing the present invention in detail, a number of terms will be defined. As used herein, the singular forms "a," "an", and "the" include plural referents unless the context clearly dictates otherwise.

As used herein, the term "polypeptide" refers to a compound of a single chain or a complex of two or more chains of amino acid residues linked by peptide bonds. The chain(s) may be of any length. A protein is a polypeptide and the terms are used synonymously. Also included within the scope of the invention are functionally equivalent variants and fragments of FIV polypeptides. The polypeptide is capable of binding one or more antibodies specific for the polypeptide.

Polypeptides derived from FIV include any region of the of the FIV proteome including for example, portions of the gag and env regions and mimitopes thereof. U.S. Pat. Nos. 5,648,209, 5,591,572, and 6,458,528, which are incorporated by reference herein in their entirety, describe FIV polypeptides derived from the FIV env and gag proteins. These peptides, and others like them, from the env and gag proteins, are suitable for use in the methods of the present invention. Examples of a suitable env polypeptides include the following:

ELGSNQNQFFSKVPPELWKRYN<u>KSKSKSKSK</u>NRWEW [SEQ ID NO: 1]

RPDFESEKC

CNRWEWRPDFESEK<u>SKSKSKS</u>MQELGSNQNQFFSKV [SEQ ID NO: 2]

PPELWKRYN

SEQ ID NO: 1 is a trimeric sequence; the first monomer is the native FIV env sequence, amino acids 696-717 with C to S, I to V, L to P, and T to K substitutions; the second monomer (underline) is a KS linker; the third monomer is the native FIV surface env protein, amino acids 396-408 with a C-terminal C addition. In one aspect of the invention, the length of the KS linker is varied from 2-20 amino acids.

SEQ ID NO:2 is a trimeric sequence; first monomer is the native FIV env protein, amino acids 396-408 with an N-terminal C addition; the second monomer (underline) is a KS linker; the third monomer is native FIV env protein, amino acids 694-717, with C to S, I to V, L to P, and T to K substitutions. In one aspect of the invention, the length of the KS linker is varied from 2-20 amino acids.

"Binding specificity" or "specific binding" refers to the substantial recognition of a first molecule for a second molecule, for example a polypeptide and a polyclonal or monoclonal antibody, or an antibody fragment (e.g. a Fv, single chain Fv, Fab', or F(ab')$_2$ fragment) specific for the polypeptide.

"Substantial binding" or "substantially bind" refer to an amount of specific binding or recognizing between molecules in an assay mixture under particular assay conditions. In its broadest aspect, substantial binding relates to the difference between a first molecule's incapability of binding or recognizing a second molecule, and the first molecules capability of binding or recognizing a third molecule, such that the difference is sufficient to allow a meaningful assay to be conducted distinguishing specific binding under a particular set of assay conditions, which includes the relative concentrations of the molecules, and the time and temperature of an incubation. In another aspect, one molecule is substantially incapable of binding or recognizing another molecule in a cross-reactivity sense where the first molecule exhibits a reactivity for a second molecule that is less than 25%, preferably less than 10%, more preferably less than 5% of the reactivity exhibited toward a third molecule under a particular set of assay conditions, which includes the relative concentration and incubation of the molecules. Specific binding can be tested using a number of widely known methods, e.g., an immunohistochemical assay, an enzyme-linked immunosorbent assay (ELISA), a radioimmunoassay (RIA), or a western blot assay.

Animals infected with FIV are felids, which is to be understood to include all members of the order Felidae, including domestic cats, lions, tigers, jaguars, leopards, puma, ocelots, etc. As used herein, the terms "felid," "cat" or "animal" is a reference to all felids.

A "biological sample" refers to a sample from an animal subject including saliva, whole blood, serum, plasma or other sample known to contain FIV antibodies An "antibody that is a significant component of an animal's immune response to a FIV vaccine" refers to an antibody that is elicited as the result of a vaccination with a FIV vaccine. These antibodies may be identical to or similar to antibodies elicited as the result of a natural FIV infection. A successful vaccination produces a measurable level of the antibody that is a significant component of the FIV vaccine.

Vaccines for FIV are described, for example, in U.S. Pat. Nos. 6,667,295, 5,833,993, 6,447,993, 6,254,872 and 6,544,528, and published U.S. Patent Application 20040096460, each of which is incorporated herein by reference in their entirety. U.S. Pat. Nos. 6,447,993 and 6,254,872 describe vaccines that are prepared from cell free-viral isolates of different FIV subtypes or a combination of cell lines each infected with different prototype FIV virus from a different subtype. U.S. Pat. No. 5,833,933 describes vaccines containing DNA sequences encoding FIV gag protein and FIV env protein. These vaccines include an expression system for expressing the sequences. One available vaccine is FEL-O-VAX® FTV vaccine (Fort Dodge Animal Health, Overland Park, Kans.).

Biological samples from animals that have been vaccinated against an FIV infection have the potential for producing a positive result in a test for an FIV infection due to the presence of antibodies produced by the animal in response to the vaccine. In one aspect, the invention provides for a method of distinguishing between animals that have been naturally infected with FIV and animals that have not been infected or have been vaccinated against an FIV infection. The method includes contacting a biological sample from the animal with a polypeptide derived from an FIV that does not substantially bind to an antibody that is a significant component of the animal's antibody response to an FIV vaccine.

In another aspect, the invention includes a method of determining whether a cat has not been infected by FIV and has not been vaccinated against FIV. A biological sample from a cat is analyzed to detect antibodies against a polypeptide, derived from FIV env and/or gag. It is then determined that the animal has not been infected and has not been or vaccinated by determining the absence of such antibodies.

In some instances, during an initial phase following a vaccination, an animal may temporarily (transiently) produce lower levels of certain antibodies to specific FIV polypeptides that are elements of a vaccine, as compared to those produced in response to a natural infection. These antibody levels taper off after a period of time to the point that antibody to these polypeptides is not detected after the initial phase. Generally, this amount of time is about ten to twelve weeks, but will vary between species and individual subject animals. Transient antibodies are not a significant component of the animal's immune response to the vaccine.

For example, the development of FIV antibodies in an animal against a vaccine is dependent upon the vaccine. For example, it has been found that animals test seropositive for FIV antibodies against p24 (gag) about two to four weeks after vaccination with the FEL-O-VAX® vaccine. However, animals so vaccinated do not generate persistent levels of antibodies against one or more regions of the env protein, even though this protein was included as an element of the vaccine. In contrast, naturally infected animals typically generate persistent levels of antibodies to both FIV gag and env proteins.

The differences in the immune response between animals that are vaccinated and animals that are naturally infected provide a means for determining whether an animal has been vaccinated or is naturally infected. Using the method of the invention, animals that have been naturally infected with FIV can be distinguished from animals that have not been infected or have been vaccinated against an FIV infection. Accordingly, the detection of the substantial binding between a polypeptide derived from FIV and an antibody that is not a significant component of an animal's immune response to a vaccine can indicate a natural infection. The relative absence of such binding can indicate vaccination or no infection. In addition, a second, separate antibody capture reagent can be included in the test that substantially binds to antibodies produced in response to vaccination and/or natural infection, such as p15 or p24 proteins. As such, various combinations of separate capture reagents can lead to a determination of the vaccination and/or infection status of the test subject.

For example, FIV gag proteins p15 and p24 may be immunogenic components of a killed whole virus FIV vaccine. It is expected that these components elicit a persistent antibody response when administered to an animal. On the other hand, some vaccines may not include immunologically significant quantities of FIV env protein or, this protein has been altered in the process of virus inactivation, or presentation of this protein by vaccination differs from that for natural infection to a point where antibodies produced thereto, if any, are detected for a period of time less than antibodies to p15 and p24. Thus, while during the initial phase following vaccination, an animal may transiently produce low levels of such antibodies that bind to env proteins, any such antibody production declines over a period of time and is not detected after about 12 weeks. In this example, the transiently produced antibodies are not a significant component of the animal's immune response to the vaccine after a period of time.

Given that the production of detectable antibodies that are directed toward specific FIV env polypeptides usually drops off after about 12 weeks from completion of vaccination, in one aspect of the invention the biological sample is obtained from the animal that has not received an FIV vaccine within about the prior 12 weeks. If the vaccination status is unknown and the test indicates infection (based on a reaction with the antibody capture protein), a retest after an additional 12 weeks can be recommended.

Differences in the immune response between vaccinated animals and naturally infected animals, such as specific antibody levels and/or kinetic parameters for antibody-antigen binding reactions (e.g., affinities, avidities), should be considered in the design of an assay for distinguishing between vaccinated and infected animals. Differences in immune response can be significant such that even after the initial phase following a vaccination, an animal may persistently produce lower levels of antibodies to specific FIV polypeptides, and/or antibodies with different binding properties as compared to those antibodies produced in response to a natural infection.

The method of the invention can be optimized in many ways and one of skill in the art could simultaneously adjust the sample dilutions, reagent concentrations, incubation temperatures and times used in the method to accomplish a differential detection of serum having antibodies to an FIV infection or vaccination. For instance, at optimized sample dilution and other conditions for an immunoassay for antibodies to specific polypeptides, samples from vaccinated animals may, for one specific FIV polypeptide, give a negative assay result and samples from infected animals will give a positive assay result. For a second FIV polypeptide, both samples may give a positive result.

In one aspect of the invention, the proteins are immobilized on a suitable solid support. The biological sample is brought into contact with the protein, to which the anti-FIV antibodies bind, if such antibodies are present in the sample. The binding may be detected by any suitable means, e.g., enzymes, radionuclides, particulates or fluorescent labels. In a suitable embodiment, the detection reagent can be associated with a protein that is the same or similar to that which is used to capture anti-FIV antibodies (if present).

In another aspect, the method is directed to a test device to determine whether a cat has been vaccinated for FIV or naturally infected with FIV. A method of using the test device includes providing a test device having an FIV env protein and a separate FIV gag protein. The device can be used to test a biological sample from a cat by contacting the device with the biological sample. Upon reading the device, the detection of the binding of an antibody to the gag protein (a positive result on the gag protein) indicates the cat has been naturally infected with FIV or vaccinated against FIV. A concurrent positive result on the env protein indicates natural infection (or, perhaps a transient post vaccination response), while a concurrent negative result on the env protein indicates vaccination. The following table summarizes the above:

|  | gag protein | env protein |
|---|---|---|
| No vaccination or infection | – | – |
| Vaccination | + | – |
| Potential Recent Vaccination | + | + |
| Infection | + | + |
| Infection and Vaccination | + | + |

The polypeptides used in the invention contain at least six amino acids, usually at least nine amino acids, and more usually twelve or more amino acids found within one of the natural FIV proteins and mimitopes and functionally equivalent variants thereof.

"Functional equivalent" or "Functionally equivalent" refers to polypeptides related to or derived from the native FIV envelope (env) and viral core (gag) polypeptide sequences where the amino acid sequence has been modified by a single or multiple amino acid substitution, insertion, deletion, and also sequences where the amino acids have been chemically modified, such as amino acid analogs, but which nonetheless retain substantially equivalent function. Functionally-equivalent variants may occur as natural biological variations or may be prepared using known techniques such as chemical synthesis, site-directed mutagenesis, random mutagenesis, or enzymatic cleavage and/or ligation of amino acids. Thus, modification of the amino-acid sequence to obtain variant sequences may occur so long as the function of the polypeptide is not affected.

FIV functionally-equivalent variants within the scope of the invention may comprise conservatively substituted sequences, meaning that one or more amino acid residues of the FIV polypeptide are replaced by different residues that do not alter the secondary and/or tertiary structure of the FIV polypeptide. Such substitutions may include the replacement of an amino acid by a residue having similar physicochemical properties, such as charge density, size, configuration, or hypdrophilicity/hydrophobicity. For purposes of example only, such substitutions could include substituting one aliphatic residue (Ile, Val, Leu, or Ala) for another, or substitution of basic residues Lys and Arg, acidic residues Glu and Asp, amide residues Gln and Asn, hydroxyl residues Ser and Tyr, or aromatic residues Phe and Tyr. Conservative variants can generally be identified by modifying a polypeptide sequence of the invention and evaluating the antigenic activity of the modified polypeptide using, for example, an immunohistochemical assay, an enzyme-linked immunosorbent assay (ELISA), a radioimmunoassay (RIA), or a western blot assay. Further information regarding the making of phenotypically silent amino acid exchanges may be found in Bowie et al., *Science* 247:1306-1310 (1990).

Examples of functional equivalents of SEQ ID NOS: 1 and 2 are shown here with a description of the various modifications to the peptides.

| SEQ ID NO: | Sequence | Description |
|---|---|---|
| 3 | CWEWRPDFESER<u>ELGSNQ</u><br><u>NQFFSK</u>SFFQNQNSGL<u>EL</u><br><u>GSNQNQFFSK</u> | Multimer sequence; first monomer comprising native FIV env protein, amino acids 398-408, N-terminal C addition, K to R substitution; second monomer (underline) comprising native FIV env protein, amino acids 696-707, C to S substitutions; third monomer comprising inverted native FIV env protein, amino acids 706-697, C to S substitutions; fourth monomer (underline) comprising native FIV env protein, amino acids 696-706, C to S substitutions |
| 4 | CNRWDWRPDFESKKS<u>KTA</u><br><u>FAMQELGSNQNQFFSKIP</u><br><u>LELWTR</u> | Dimeric sequence; first monomer comprising native FIV env protein, amino acids 396-408, N-terminal C addition, E to W, E to K substitution, SK addition; second monomer (underline) comprising native FIV env protein, amino acids 690-715, C to S, K to T substitutions |
| 5 | CNRWEWRPDFESEK<u>MQEL</u><br><u>GSNQNQFFSKVPPELWKR</u><br><u>YN</u> | Dimeric sequence; first monomer comprising native FIV env protein, amino acids 396-408, N-terminal C addition; second monomer (underline) comprising native FIV env protein, |

-continued

| SEQ ID NO: | Sequence | Description |
|---|---|---|
| | | amino acids 694-717, C to S, I to V, L to P, T to K substitutions |

Additional variants are also contemplated within the scope of the invention, and such variants include amino and/or carboxyl terminal fusions, for example achieved by addition of amino acid sequences of any number of residues, as well as intrasequence insertion of one or more amino acids. For example, amino acid sequences added may be those derived from the whole or parts of other polypeptides or proteins, or may be those provided in the corresponding positions in the FIV envelope or viral protein. Longer peptides may comprise multiple copies of one or more of the polypeptide sequences. Moreover, multiple copies of the polypeptides may be coupled to a polyamino acid backbone, such as a polylysine backbone to form multiple antigen peptides (MAPs).

Deletional amino acid sequence variants are those in which one or more amino acid residues are removed from the sequence. Insertional variants exist when one or more amino acids are integrated into a predetermined site in the protein, although random insertion is an option with suitable screening of the resulting product. In all cases, these and other FIV variants used retain substantially the same antigenicity of the FIV polypeptides. Other variants are also contemplated, including those where the amino acid substitutions are made in the area outside the antibody recognition regions of the protein. Fusion proteins comprising two or more polypeptide sequences of FIV are also within the scope of the invention provided the sequences provide the appropriate antigenicity. Such polypeptides will generally correspond to at least one epitope or mimitope that is characteristic of FIV. By characteristic, it is meant that the epitope or mimitope will allow immunologic detection of antibody directed to FIV in a physiological sample with reasonable assurance. Usually, it will be desirable that the epitope or mimitope, variant or fusion protein be immunologically distinct from (i.e., not cross-reactive with antibodies which recognize) viruses other than FIV.

An antigenically active variant differs by about, for example, 1, 2, 3, 5, 6, 10, 15 or 20 amino acid residues from SEQ ID NOS: 1 and 2, such as those shown in SEQ ID NOS: 3-10, or a fragment thereof. Where this comparison requires alignment the sequences are aligned for maximum homology. Deletions, insertions, substitutions, repeats, inversions or mismatches are considered differences. The differences are, preferably, differences or changes at a non-essential residue or a conservative substitution. The site of variation can occur anywhere in the polypeptide, as long as the resulting variant polypeptide is antigenically substantially similar to SEQ ID NOS: 1 and 2, such as, for example, the variations shown in SEQ ID NOS: 3-10 (see Tables 3 and 4). Exemplary functionally-equivalent variants include those displaying 50% or more amino acid homology. Preferably, such homology is 60%, 70%, or greater than 80%. However, such variants may display a smaller percentage of homology overall and still fall within the scope of the invention where they have conserved regions of homology.

In some cases, one or more cysteine residues may be added to the termini of the polypeptides in order to facilitate specific carrier linkage or to permit disulphide bonding to mimic antigenic loops and thus increase the antigenicity. Moreover, a fatty acid or hydrophobic tail may be added to the peptides to facilitate incorporation into delivery vehicles and to increase antigenicity.

Some examples of monomers that can be used to produce variants of the polypeptides of SEQ ID NOS: 1-5 are as follows:

| SEQ ID NO | Sequence | Description |
|---|---|---|
| 6 | TAFAMQELGSNQNQFFSK | Native FIV env protein, amino acids 690-707, C to S substitutions |
| 7 | TAFAMQELGCNQQQFFCA | Native FIV env protein, amino acids 690-707, N to Q, K to A substitutions |
| 8 | YTAFAMQEIGCNQNQFFCA | Native FIV env protein, amino acids 689-707, L to I, K to A substitutions |
| 9 | ELGCNQNQFFCK | Native FIV env protein, amino acids 696-707 |
| 10 | CEGSNQNQFFSK | Native FIV env protein, amino acids 696-707, N-terminal C addition, L deletion, C to S substitutions |

In yet another aspect, the invention provides novel polypeptides. These polypeptides may be used, for example, as detection reagents in kits or in vaccines. One such polypeptide has the following formula $[(P^1)_a-(L^1)_b-(P^2)_c]_n$, wherein $P^1$ is a polypeptide that is the native, or an antigenic fragment and functionally-equivalent variant of native FIV env peptides 696-717, and $P^2$ is a polypeptide that is the native, or an antigenic fragment and functionally-equivalent variant of native FIV env protein, amino acids 396-408. Either $P^1$ or $P^2$ can be inverted. For example, $P^1$ can be, for example, any of SEQ ID NOs. 6-10, or one of

| | |
|---|---|
| ELGSNQNQFFSKVPPELWKRYN, | [SEQ ID NO: 11] |
| MQELGSNQNQFFSPPELWKRYN, | [SEQ ID NO: 12] |
| ELGSNQNQFFSK, | [SEQ ID NO: 13] |
| LGSNQNQFFS, and | [SEQ ID NO: 14] |
| TAFAMQELGSNQNQFFSKIPLELWTR, | [SEQ ID NO: 15] | and P² can be, for example, one of

| NRWEWRPDFESEKC, | [SEQ ID NO: 16] |
| CNRWEWRPDFESEK, | [SEQ ID NO: NO: 17] |
| CWEWRPDFESER, and | [SEQ ID NO: 18] |
| CNRWDWRPDFESKK, | [SEQ ID NO: 19] | where either P¹ and/or P² is inverted. L¹ is a linker polypeptide consisting of 2-20 alternatively repeating S and K peptides, beginning and ending with either S or K, and where a, c and n may independently be an integer from 1 to 3, and b may be an integer from 0 to 1.

The FIV polypeptides used as detection reagents may be natural, i.e., including the entire FIV protein or fragments thereof isolated from a natural source, or may be synthetic. The natural proteins may be isolated from the whole FIV virus by conventional techniques, such as affinity chromatography. Polyclonal or monoclonal antibodies may be used to prepare a suitable affinity column by well-known techniques.

Proteins that are immunologically cross-reactive with a natural FIV protein can be chemically synthesized. For example, polypeptides having fewer than about 100 amino acids, more usually fewer than about 80 amino acids, and typically fewer than about 50 amino acids, may be synthesized by the well-known Merrifield solid-phase synthesis method where amino acids are sequentially added to a growing chain. Merrifield, 1963, J. Am. Chem. Soc., 85:2149-2156). Recombinant proteins can also be used. These proteins may be produced by expression in cultured cells of recombinant DNA molecules encoding a desired portion of the FIV genome. The portion of the FIV genome may itself be natural or synthetic, with natural genes obtainable from the isolated virus by conventional techniques. Of course, the genome of FIV is RNA, and it will be necessary to transcribe the natural RNA into DNA by conventional techniques employing reverse transcriptase. Polynucleotides may also be synthesized by well-known techniques. For example, short single-stranded DNA fragments may be prepared by the phosphoramidite method described by Beaucage and Carruthers, 1981, Tett. Letters 22:1859-1862. Double-stranded fragments may then be obtained either by synthesizing the complementary strand and then annealing the strands together under appropriate conditions, or by adding the complementary strand using DNA polymerase with an appropriate primer sequence.

The natural or synthetic DNA fragments coding for the desired FIV protein or fragment may be incorporated in a DNA construct capable of introduction to and expression in in vitro cell culture. Usually, the DNA constructs will be suitable for replication in a unicellular host, such as yeast or bacteria. They may also be intended for introduction and integration within the genome of cultured mammalian or other eukaryotic cells. DNA constructs prepared for introduction into bacteria or yeast will include a replication system recognized by the host, the FIV DNA fragment encoding the desired polypeptide product, transcriptional and translational initiation regulatory sequences joined to the 5'-end of the FIV DNA termination regulatory sequences joined to the 3'-end of the fragment. The transcriptional regulatory sequences will include a heterologous promoter that is recognized by the host. Conveniently, a variety of suitable expression vectors are commercially available for a number of hosts.

To be useful in the detection methods of the present invention, the polypeptides are obtained in a substantially pure form, that is, typically from about 50% w/w or more purity, substantially free of interfering proteins and contaminants. Preferably, the FIV polypeptides are isolated or synthesized in a purity of at least 80% w/w, and more preferably, in at least about 95% w/w purity. Using conventional protein purification techniques, homogeneous polypeptide compositions of at least about 99% w/w purity can be obtained. For example, the proteins may be purified by use of the antibodies described hereinafter using the immunoabsorbant affinity columns described hereinabove.

The method of the invention may be accomplished using immunoassay techniques well known to those of skill in the art, including, but not limited to, using microplates and lateral flow devices. In one embodiment, an FIV protein is immobilized on a solid support at a distinct location. Detection of protein-antibody complexes on the solid support can be by any means known in the art. For example, U.S. Pat. No. 5,726,010, which is incorporated herein by reference in its entirety, describes an example of a lateral flow device, the SNAP® immunoassay device (IDEXX Laboratories), useful in the present invention. Colloidal particle based tests can also be used, such as the commercially available WITNESS® FIV diagnostic test (Synbiotics Corporation, Lyon, France).

Immobilization of one or more analyte capture reagents, e.g., FIV proteins, onto a device or solid support is performed so that an analyte capture reagent will not be washed away by the sample, diluent and/or wash procedures. One or more analyte capture reagents can be attached to a surface by physical adsorption (i.e., without the use of chemical linkers) or by chemical binding (i.e., with the use of chemical linkers). Chemical binding can generate stronger attachment of specific binding substances on a surface and provide defined orientation and conformation of the surface-bound molecules.

Another embodiment of the invention provides a device that is suitable for a lateral flow assay. For example, a test sample is added to a flow matrix at a first region (a sample application zone). The test sample is carried in a fluid flow path by capillary action to a second region of the flow matrix where a label capable of binding and forming a first complex with an analyte in the test sample. The first complex is carried to a third region of the flow matrix where an FIV protein is immobilized at a distinct location. A second complex is formed between an immobilized protein and the first complex including the antibody from the sample. For example, a first complex comprising a gold sol particle and an FIV protein bound to an FIV antibody will specifically bind and form a second complex with a second immobilized FIV protein or with a second antibody directed to feline antibodies. The label that is part of the second complex can be directly visualized.

In another aspect, the invention includes one or more labeled specific binding reagents that can be mixed with a test sample prior to application to a device for of the invention. In this case it is not necessary to have labeled specific binding reagents deposited and dried on a specific binding reagent pad in the device. A labeled specific binding reagent, whether added to a test sample or pre-deposited on the device, can be for example, a labeled FIV protein that specifically binds an antibody for FIV.

Any or all of the above embodiments can be provided as a kit. In one particular example, such a kit would include a device complete with specific binding reagents (e.g., a non-immobilized labeled specific binding reagent and an immobilized analyte capture reagent) and wash reagent, as well as detector reagent and positive and negative control reagents, if desired or appropriate. In addition, other additives can be included, such as stabilizers, buffers, and the like. The relative amounts of the various reagents can be varied, to provide for concentrations in solution of the reagents that substantially optimize the sensitivity of the assay. Particularly, the reagents can be provided as dry powders, usually lyophilized, which on dissolution will provide for a reagent solution having the appropriate concentrations for combining with a sample.

An FIV protein can be an immobilized analyte capture reagent in a reaction zone (solid phase). A second analyte capture reagent, i.e. a second FIV protein, that has been conjugated to a label, can either be added to the sample before the sample is added to the device, or the second analyte capture reagent can be incorporated into the device. For example the labeled specific binding reagent can be deposited and dried on a fluid flow path that provides fluid communication between the sample application zone and the solid phase. Contact of the labeled specific binding reagent with the fluid sample results in dissolution of the labeled specific binging reagent.

The device may also include a liquid reagent that transports unbound material (e.g., unreacted fluid sample and unbound specific binding reagents) away from the reaction zone (solid phase). A liquid reagent can be a wash reagent and serve only to remove unbound material from the reaction zone, or it can include a detector reagent and serve to both remove unbound material and facilitate analyte detection. For example, in the case of a specific binding reagent conjugated to an enzyme, the detector reagent includes a substrate that produces a detectable signal upon reaction with the enzyme-antibody conjugate at the reactive zone. In the case of a labeled specific binding reagent conjugated to a radioactive, fluorescent, or light-absorbing molecule, the detector reagent acts merely as a wash solution facilitating detection of complex formation at the reactive zone by washing away unbound labeled reagent.

Two or more liquid reagents can be present in a device, for example, a device can comprise a liquid reagent that acts as a wash reagent and a liquid reagent that acts as a detector reagent and facilitates analyte detection.

A liquid reagent can further include a limited quantity of an "inhibitor", i.e., a substance that blocks the development of the detectable end product. A limited quantity is an amount of inhibitor sufficient to block end product development until most or all excess, unbound material is transported away from the second region, at which time detectable end product is produced.

The following are provided for exemplification purposes only and are not intended to limit the scope of the invention described in broad terms above. All references cited in this disclosure are incorporated herein by reference.

EXAMPLES

Example 1

Eight cats testing negative for FIV with the SNAP® FeLV Ag/FIV Ab test kits were vaccinated with FEL-O-VAX® FIV vaccine, Fort Dodge Animal Health, Fort Dodge Iowa. This vaccine is produced from multiple strains of the whole killed FIV virus. The cats were vaccinated following the manufacturer's directions at day 0, 14, and 28. Two cats testing negative for FIV were not vaccinated and were included as controls for this study.

Blood samples were obtained from each of the ten cats in the vaccination study at day zero and every seven days for 12 weeks and stored frozen until testing. In addition, blood samples from FIV negative cats and cats naturally infected with FIV, confirmed FIV Ab negative or positive by a western immunoblot confirmatory test, were also tested.

Sample testing was accomplished using a SNAP® immunoassay device, which provides a solid phase with reversible, chromatographic flow of sample, and automatic, sequential flow of wash and enzyme substrate solutions as described in U.S. Pat. No. 5,726,010.

For the SNAP® device, FIV gag p24 (recombinant) and an FIV env 696-707 with additional N-terminal cysteine—CEL-GCNQNQFFCK [SEQ ID NO:20]—proteins were deposited to form a single antibody capture spot on the solid phase. A negative control reagent was deposited to form a negative control spot and a positive control reagent was deposited to form a positive control spot on the solid phase of the SNAP® device. The gag or env proteins were chemically conjugated to the enzyme horseradish peroxidase and provided in a solution consisting of a buffer, detergent, and animal serum components.

Serum samples were combined with either gag or env protein-enzyme conjugate solution, and applied to the SNAP® device. Following a short incubation period, the device was activated. Color development on the positive control spot indicated the test was valid. Color development on the sample spot greater than color development on the negative control spot indicated the presence of antigen in the sample and was scored as a positive test result. Test results were determined visually and are shown in Table 1.

TABLE 1

| Animal ID | Status | Day | gag Ab test result (visual) | env Ab test result (visual) |
|---|---|---|---|---|
| NV1 | not vaccinated, not infected | 0 | NEG | NEG |
| NV1 | not vaccinated, not infected | 7 | NEG | NEG |
| NV1 | not vaccinated, not infected | 14 | NEG | NEG |
| NV1 | not vaccinated, not infected | 21 | NEG | NEG |
| NV1 | not vaccinated, not infected | 28 | NEG | NEG |
| NV1 | not vaccinated, not infected | 35 | NEG | NEG |
| NV1 | not vaccinated, not infected | 42 | NEG | NEG |
| NV1 | not vaccinated, not infected | 49 | NEG | NEG |
| NV1 | not vaccinated, not infected | 56 | NEG | NEG |
| NV1 | not vaccinated, not infected | 63 | NEG | NEG |
| NV1 | not vaccinated, not infected | 70 | NEG | NEG |
| NV1 | not vaccinated, not infected | 77 | NEG | NEG |
| NV1 | not vaccinated, not infected | 84 | NEG | NEG |
| NV2 | not vaccinated, not infected | 0 | NEG | NEG |
| NV2 | not vaccinated, not infected | 7 | NEG | NEG |
| NV2 | not vaccinated, not infected | 14 | NEG | NEG |
| NV2 | not vaccinated, not infected | 21 | NEG | NEG |
| NV2 | not vaccinated, not infected | 28 | NEG | NEG |
| NV2 | not vaccinated, not infected | 35 | NEG | NEG |
| NV2 | not vaccinated, not infected | 42 | NEG | NEG |
| NV2 | not vaccinated, not infected | 49 | NEG | NEG |
| NV2 | not vaccinated, not infected | 56 | NEG | NEG |
| NV2 | not vaccinated, not infected | 63 | NEG | NEG |
| NV2 | not vaccinated, not infected | 70 | NEG | NEG |
| NV2 | not vaccinated, not infected | 77 | NEG | NEG |
| NV2 | not vaccinated, not infected | 84 | NEG | NEG |
| V1 | vaccinated, not infected | 0 | NEG | NEG |
| V1 | vaccinated, not infected | 7 | NEG | NEG |
| V1 | vaccinated, not infected | 14 | NEG | NEG |
| V1 | vaccinated, not infected | 21 | POS | NEG |
| V1 | vaccinated, not infected | 28 | POS | NEG |
| V1 | vaccinated, not infected | 35 | POS | POS |
| V1 | vaccinated, not infected | 42 | POS | NEG |
| V1 | vaccinated, not infected | 49 | POS | NEG |
| V1 | vaccinated, not infected | 56 | POS | NEG |
| V1 | vaccinated, not infected | 63 | POS | NEG |
| V1 | vaccinated, not infected | 70 | POS | NEG |
| V1 | vaccinated, not infected | 77 | POS | NEG |
| V1 | vaccinated, not infected | 84 | POS | NEG |
| V2 | vaccinated, not infected | 0 | NEG | NEG |
| V2 | vaccinated, not infected | 7 | NEG | NEG |
| V2 | vaccinated, not infected | 14 | NEG | NEG |
| V2 | vaccinated, not infected | 21 | NEG | NEG |

TABLE 1-continued

| Animal ID | Status | Day | gag Ab test result (visual) | env Ab test result (visual) |
|---|---|---|---|---|
| V2 | vaccinated, not infected | 28 | NEG | NEG |
| V2 | vaccinated, not infected | 35 | POS | NEG |
| V2 | vaccinated, not infected | 42 | POS | NEG |
| V2 | vaccinated, not infected | 49 | POS | NEG |
| V2 | vaccinated, not infected | 56 | POS | NEG |
| V2 | vaccinated, not infected | 63 | POS | NEG |
| V2 | vaccinated, not infected | 70 | POS | NEG |
| V2 | vaccinated, not infected | 77 | POS | NEG |
| V2 | vaccinated, not infected | 84 | POS | NEG |
| V3 | vaccinated, not infected | 0 | NEG | NEG |
| V3 | vaccinated, not infected | 7 | NEG | NEG |
| V3 | vaccinated, not infected | 14 | NEG | NEG |
| V3 | vaccinated, not infected | 21 | NEG | NEG |
| V3 | vaccinated, not infected | 28 | NEG | NEG |
| V3 | vaccinated, not infected | 35 | POS | NEG |
| V3 | vaccinated, not infected | 42 | POS | NEG |
| V3 | vaccinated, not infected | 49 | POS | NEG |
| V3 | vaccinated, not infected | 56 | POS | NEG |
| V3 | vaccinated, not infected | 63 | POS | NEG |
| V3 | vaccinated, not infected | 70 | POS | NEG |
| V3 | vaccinated, not infected | 77 | POS | NEG |
| V3 | vaccinated, not infected | 84 | POS | NEG |
| V4 | vaccinated, not infected | 0 | NEG | NEG |
| V4 | vaccinated, not infected | 7 | NEG | NEG |
| V4 | vaccinated, not infected | 14 | POS | NEG |
| V4 | vaccinated, not infected | 21 | POS | NEG |
| V4 | vaccinated, not infected | 28 | POS | NEG |
| V4 | vaccinated, not infected | 35 | POS | NEG |
| V4 | vaccinated, not infected | 42 | POS | NEG |
| V4 | vaccinated, not infected | 49 | POS | NEG |
| V4 | vaccinated, not infected | 56 | POS | NEG |
| V4 | vaccinated, not infected | 63 | POS | NEG |
| V4 | vaccinated, not infected | 70 | POS | NEG |
| V4 | vaccinated, not infected | 77 | POS | NEG |
| V4 | vaccinated, not infected | 84 | POS | NEG |
| V5 | vaccinated, not infected | 0 | NEG | NEG |
| V5 | vaccinated, not infected | 7 | NEG | NEG |
| V5 | vaccinated, not infected | 14 | NEG | NEG |
| V5 | vaccinated, not infected | 21 | POS | POS |
| V5 | vaccinated, not infected | 28 | POS | NEG |
| V5 | vaccinated, not infected | 35 | POS | NEG |
| V5 | vaccinated, not infected | 42 | POS | NEG |
| V5 | vaccinated, not infected | 49 | POS | NEG |
| V5 | vaccinated, not infected | 56 | POS | NEG |
| V5 | vaccinated, not infected | 63 | POS | NEG |
| V5 | vaccinated, not infected | 70 | POS | NEG |
| V5 | vaccinated, not infected | 77 | POS | NEG |
| V5 | vaccinated, not infected | 84 | POS | NEG |
| V6 | vaccinated, not infected | 0 | NEG | NEG |
| V6 | vaccinated, not infected | 7 | NEG | NEG |
| V6 | vaccinated, not infected | 14 | NEG | NEG |
| V6 | vaccinated, not infected | 21 | POS | NEG |
| V6 | vaccinated, not infected | 28 | POS | NEG |
| V6 | vaccinated, not infected | 35 | POS | POS |
| V6 | vaccinated, not infected | 42 | POS | NEG |
| V6 | vaccinated, not infected | 49 | POS | NEG |
| V6 | vaccinated, not infected | 56 | POS | NEG |
| V6 | vaccinated, not infected | 63 | POS | NEG |
| V6 | vaccinated, not infected | 70 | POS | NEG |
| V6 | vaccinated, not infected | 77 | POS | NEG |
| V6 | vaccinated, not infected | 84 | POS | NEG |
| V7 | vaccinated, not infected | 0 | NEG | NEG |
| V7 | vaccinated, not infected | 7 | NEG | NEG |
| V7 | vaccinated, not infected | 14 | NEG | NEG |
| V7 | vaccinated, not infected | 21 | POS | NEG |
| V7 | vaccinated, not infected | 28 | POS | NEG |
| V7 | vaccinated, not infected | 35 | POS | NEG |
| V7 | vaccinated, not infected | 42 | POS | POS |
| V7 | vaccinated, not infected | 49 | POS | POS |
| V7 | vaccinated, not infected | 56 | POS | NEG |
| V7 | vaccinated, not infected | 63 | POS | NEG |
| V7 | vaccinated, not infected | 70 | POS | NEG |
| V7 | vaccinated, not infected | 77 | POS | NEG |
| V7 | vaccinated, not infected | 84 | POS | NEG |
| V8 | vaccinated, not infected | 0 | NEG | NEG |
| V8 | vaccinated, not infected | 7 | NEG | NEG |
| V8 | vaccinated, not infected | 14 | POS | NEG |
| V8 | vaccinated, not infected | 21 | POS | NEG |
| V8 | Vaccinated, not infected | 28 | POS | NEG |
| V8 | Vaccinated, not infected | 35 | POS | NEG |
| V8 | Vaccinated, not infected | 42 | POS | NEG |
| V8 | Vaccinated, not infected | 49 | POS | NEG |
| V8 | Vaccinated, not infected | 56 | POS | NEG |
| V8 | Vaccinated, not infected | 63 | POS | NEG |
| V8 | Vaccinated, not infected | 70 | POS | NEG |
| V8 | Vaccinated, not infected | 77 | POS | NEG |
| V8 | Vaccinated, not infected | 84 | POS | NEG |
| Inf1 | Not vaccinated, infected | ND | POS | POS |
| Inf2 | Not vaccinated, infected | ND | POS | POS |
| Inf3 | Not vaccinated, infected | ND | POS | POS |
| Inf4 | Not vaccinated, infected | ND | POS | POS |
| Inf5 | Not vaccinated, infected | ND | POS | POS |
| Inf6 | Not vaccinated, infected | ND | POS | POS |
| Inf7 | Not vaccinated, infected | ND | POS | POS |
| Inf8 | Not vaccinated, infected | ND | POS | POS |
| Inf9 | Not vaccinated, infected | ND | POS | POS |
| infl0 | Not vaccinated, infected | ND | POS | POS |

Example 2

Microplate ELISA analysis was performed on serum samples collected from confirmed FIV negative and infected cats, and cats vaccinated with the FEL-O-VAX® FIV vaccine in an indirect assay format with individual FIV polypeptides on the solid phase and anti-(feline IgG) peroxidase conjugate. Antibodies to FIV env were detected using these peptides as antigen reagents:

```
ELGSNQNQFFSKVPPELWKRYNKSKSKSKSKNRW   [SEQ ID NO: 1]
EWRPDFESEKC

CNRWEWRPDFESEKSKSKSKSMQELGSNQNQFFS   [SEQ ID NO: 2]
KVPPELWKRYN

CWEWRPDFESERELGSNQNQFFSKSFFQNQNSGL   [SEQ ID NO: 3]
ELGSNQNQFFSK

CNRWDWRPDFESKKSKTAFAMQELGSNQNQFFSK   [SEQ ID NO: 4]
IPLELWTR

CNRWEWRPDFESEKMQELGSNQNQFFSKVPPELW   [SEQ ID NO: 5]
KRYN

CEGSNQNQFFSK                         [SEQ ID NO: 10]
```

The polypeptides were synthesized using a commercial instrument and following the manufacturer's instructions. Polypeptide stocks were prepared at 5 mg/ml in DMSO. The polypeptides were then coated on microplate wells (peptide @ 10 ug/ml in 50 mM Tris-HCl pH 7.4, 100 ul/well). The plates were then blocked/overcoated with 2% Tween-20/ 2.5% sucrose, allowed to dry in mylar bags with desiccant.

For the assays, feline serum samples (100 ul/well, diluted 1/1000 in 50% fetal bovine serum) were added to the wells and the plates were incubated for ten minutes at room temperature. Following incubation, the microplates were washed with PBS/Tween. Goat Anti-(cat IgG):peroxidase conjugate was added to the wells (100 ul/well anti-catIgG:peroxidase diluted in 50% fetal bovine serum). The plates were incubated for another fifteen minutes at room temperature and washed a second time with PBS/Tween. Peroxidase substrate was added (100 ul/well, tetramethyl benzidine peroxidase substrate) and the plates were incubated a third time for ten minutes at room temperature. A hydrofluoric acid stop solution (50 ul/well) was added to the plates. Sample antibody binding was measured by determining peroxidase activity (colored product) with a spectrophotometer (A650 nm). Significant, substantial antibody binding for a sample is considered to be A650 nm greater than 0.200). The IDEXX PETCHEK® Anti-FIV antibody test kit was also run on these samples as a reference test. The results are shown in Table 2.

Example 3

Microplate ELISA analysis was performed as in Example 2 on serum samples collected from confirmed FIV negative and infected cats, and cats vaccinated with the FEL-O-VAX® FIV vaccine. Antibodies to FIV env were detected using these peptides as antigen reagents:

```
CNRWEWRPDFESEKSKSKSKSMQELGSNQNQFFSK    [SEQ ID NO: 2]

VPPELWKRYN

TAFAMQELGSNQNQFFSK                     [SEQ ID NO: 6]

TAFAMQELGCNQQQFFCA                     [SEQ ID NO: 7]

YTAFAMQEIGCNQNQFFCA                    [SEQ ID NO: 8]

ELGCNQNQFFCK                           [SEQ ID NO: 9]
```

Significant, substantial antibody binding for a sample is considered to be A650 nm greater than 0.200). The IDEXX PETCHEK® Anti-FIV antibody test kit was also run on these samples as a reference test. The results are reported in Tables 3.

TABLE 2

| sample | seq ID 1 A(650 nm) | seq ID 2 A(650 nm) | seq ID 3 A(650 nm) | seq ID 10 A(650 nm) | seq ID 4 A(650 nm) | seq ID 5 A(650 nm) | PetChek result |
|---|---|---|---|---|---|---|---|
| FIV infected, not vaccinated: | | | | | | | |
| 58376-274 | 1.400 | 1.944 | 1.838 | 1.370 | 1.910 | 2.109 | positive |
| JL-60 | 1.139 | 1.906 | 1.433 | 2.127 | 2.014 | 1.639 | positive |
| 21636 | 1.301 | 1.838 | 1.944 | 1.918 | 1.986 | 2.080 | positive |
| Gonzalez | 0.951 | 1.775 | 1.281 | 1.920 | 1.520 | 1.407 | positive |
| 2605 | 0.500 | 1.593 | 0.746 | 0.965 | 1.152 | 0.871 | positive |
| Stanley | 0.972 | 1.590 | 0.834 | 0.442 | 1.124 | 1.044 | positive |
| 2614 | 0.328 | 1.029 | 0.382 | 1.095 | 0.527 | 0.945 | positive |
| mean | 0.942 | 1.668 | 1.208 | 1.405 | 1.462 | 1.442 | |
| std. deviation | 0.398 | 0.314 | .582 | .615 | .558 | .520 | |
| FIV vaccinated, not infected: | | | | | | | |
| Vx 3520 D84 | 0.032 | 0.042 | 0.035 | 0.040 | 0.043 | 0.045 | positive |
| Vx 3519 D84 | 0.032 | 0.084 | 0.036 | 0.041 | 0.040 | 0.038 | positive |
| Vx 3532 D84 | 0.026 | 0.038 | 0.036 | 0.042 | 0.038 | 0.040 | positive |
| Vx SK4 D84 | 0.031 | 0.047 | 0.033 | 0.048 | 0.042 | 0.046 | positive |
| Vx G1 wk5 | 0.032 | 0.111 | 0.100 | 0.101 | 0.114 | 0.116 | positive |
| Vx G1 wk7 | 0.035 | 0.114 | 0.105 | 0.103 | 0.121 | 0.137 | positive |
| Vx G1 wk8 | 0.035 | 0.095 | 0.088 | 0.096 | 0.095 | 0.108 | positive |
| Vx G1 wk12 | 0.036 | 0.100 | 0.087 | 0.085 | 0.101 | 0.111 | positive |
| mean | 0.032 | 0.079 | 0.065 | 0.070 | 0.074 | 0.080 | |
| std. deviation | 0.003 | 0.032 | 0.033 | 0.029 | 0.037 | 0.041 | |
| FIV negative, not vaccinated: | | | | | | | |
| 2151-05H | 0.032 | 0.064 | 0.050 | 0.049 | 0.039 | 0.047 | negative |
| F6263E | 0.039 | 0.045 | 0.038 | 0.058 | 0.039 | 0.037 | negative |
| Abraham | 0.032 | 0.045 | 0.035 | 0.035 | 0.037 | 0.035 | negative |
| AWL 2002 | 0.033 | 0.041 | 0.033 | 0.072 | 0.039 | 0.051 | negative |
| 14834 | 0.030 | 0.035 | 0.024 | 0.036 | 0.038 | 0.034 | negative |
| D1606315 | 0.032 | 0.035 | 0.033 | 0.035 | 0.041 | 0.038 | negative |
| 2483-83-33 | 0.029 | 0.034 | 0.033 | 0.035 | 0.036 | 0.036 | negative |
| 2483-83-23 | 0.032 | 0.033 | 0.033 | 0.035 | 0.038 | 0.039 | negative |
| 2483-83-30 | 0.030 | 0.033 | 0.033 | 0.035 | 0.038 | 0.035 | negative |
| 2377-1-38 | 0.030 | 0.033 | 0.033 | 0.034 | 0.037 | 0.035 | negative |
| 769703 | 0.029 | 0.032 | 0.035 | 0.035 | 0.042 | 0.036 | negative |
| 2377-23-3 | 0.026 | 0.032 | 0.032 | 0.033 | 0.036 | 0.035 | negative |
| 14151 | 0.032 | 0.032 | 0.034 | 0.034 | 0.037 | 0.035 | negative |
| 768547 | 0.030 | 0.031 | 0.034 | 0.034 | 0.037 | 0.035 | negative |
| 768513 | 0.032 | 0.030 | 0.034 | 0.036 | 0.037 | 0.042 | negative |
| mean | 0.031 | 0.037 | 0.034 | 0.040 | 0.038 | 0.038 | |
| std. deviation | 0.003 | 0.009 | 0.005 | 0.011 | 0.002 | 0.005 | |

TABLE 3

| sample | seq ID 2 A(650 nm) | seq ID 6 A(650 nm) | Seq ID 7 A(650 nm) | seq ID 8 A(650 nm) | seq ID 9 A(650 nm) | PetChek result |
|---|---|---|---|---|---|---|
| FIV infected, not vaccinated: | | | | | | |
| 2689: 44 7 | 2.212 | 0.908 | 1.696 | 0.893 | 1.153 | positive |
| 197 | 2.123 | 0.687 | 1.623 | 1.590 | 1.027 | positive |
| 22488 | 2.121 | 0.802 | 1.162 | 1.663 | 1.296 | positive |
| 23804 255 | 2.065 | 0.991 | 0.829 | 1.078 | 1.036 | positive |
| 24034 283 | 1.973 | 0.663 | 1.436 | 1.318 | 1.202 | positive |
| F0-138 1/23/00 | 1.951 | 1.409 | 1.835 | 1.412 | 1.548 | positive |
| 56360 60 | 1.881 | 1.391 | 1.553 | 1.270 | 1.298 | positive |
| 57561 181 | 1.875 | 1.782 | 1.747 | 1.000 | 1.293 | positive |
| 56897 187 | 1.864 | 0.813 | 1.492 | 0.929 | 1.102 | positive |
| 21518 | 1.849 | 1.000 | 1.419 | 1.032 | 0.955 | positive |
| 58178 232 | 1.839 | 1.386 | 1.338 | 1.392 | 1.237 | positive |
| 58376 274 8/17 | 1.826 | 0.617 | 0.448 | 0.314 | 0.471 | positive |
| 23805 253 | 1.796 | 1.005 | 0.562 | 0.721 | 0.599 | positive |
| 21636 | 1.795 | 1.726 | 1.225 | 1.811 | 1.238 | positive |
| 58232 242 | 1.724 | 0.454 | 1.580 | 0.686 | 1.297 | positive |
| 23119 | 1.721 | 0.888 | 1.154 | 0.447 | 1.156 | positive |
| 57601 215 | 1.659 | 0.725 | 0.987 | 0.722 | 0.601 | positive |
| 22373 275 | 1.646 | 0.641 | 1.853 | 0.695 | 1.584 | positive |
| F9-881 | 1.574 | 0.926 | 0.587 | 1.272 | 0.589 | positive |
| 23938 323 | 1.554 | 0.635 | 1.475 | 0.999 | 1.333 | positive |
| 58036 224 | 1.418 | 1.387 | 1.218 | 0.828 | 1.102 | positive |
| 22879 | 1.332 | 0.468 | 1.117 | 0.752 | 1.055 | positive |
| F0-162 2/13/00 | 1.273 | 1.068 | 1.284 | 0.702 | 1.046 | positive |
| 23321 211 | 1.214 | 1.183 | 0.751 | 1.308 | 0.886 | positive |
| mean | 1.762 | 0.981 | 1.265 | 1.035 | 1.088 | |
| std. deviation | 0.267 | 0.371 | 0.404 | 0.385 | 0.290 | |
| FIV negative, vaccinated: | | | | | | |
| Vx C3520 D35 | 0.211 | 0.058 | 0.142 | 0.065 | 0.116 | positive |
| Vx C3511 D49 | 0.173 | 0.155 | 0.209 | 0.111 | 0.180 | positive |
| Vx C3519 D35 | 0.110 | 0.053 | 0.091 | 0.058 | 0.055 | positive |
| Vx C3517 D35 | 0.110 | 0.082 | 0.093 | 0.063 | 0.074 | positive |
| Vx SK4 D21 | 0.066 | 0.035 | 0.082 | 0.038 | 0.044 | positive |
| mean | 0.134 | 0.077 | 0.123 | 0.067 | 0.094 | |
| std. deviation | 0.058 | 0.047 | 0.054 | 0.027 | 0.055 | |
| F9-1164 | 0.061 | 0.038 | 0.054 | 0.039 | 0.036 | negative |
| 57435 272 8/17 | 0.058 | 0.039 | 0.046 | 0.035 | 0.039 | negative |
| 57975 236 | 0.048 | 0.035 | 0.040 | 0.043 | 0.036 | negative |
| 57323 174 | 0.046 | 0.046 | 0.032 | 0.042 | 0.034 | negative |
| 56728 200 | 0.045 | 0.039 | 0.049 | 0.044 | 0.042 | negative |
| 58238 251 8/14 | 0.044 | 0.031 | 0.032 | 0.033 | 0.033 | negative |
| 56956 209 | 0.044 | 0.035 | 0.049 | 0.038 | 0.036 | negative |
| F9-1638 143119 | 0.042 | 0.035 | 0.037 | 0.036 | 0.039 | negative |
| F9-1191 | 0.041 | 0.027 | 0.040 | 0.037 | 0.037 | negative |
| 57528 197 | 0.041 | 0.033 | 0.039 | 0.035 | 0.035 | negative |
| 57095 125 | 0.041 | 0.034 | 0.038 | 0.035 | 0.035 | negative |
| 56704 154 | 0.039 | 0.033 | 0.040 | 0.027 | 0.035 | negative |
| 57911 235 | 0.039 | 0.040 | 0.056 | 0.050 | 0.038 | negative |
| F9-1455 11/14/99 | 0.038 | 0.034 | 0.037 | 0.037 | 0.033 | negative |
| F0-53 1/23/00 | 0.038 | 0.035 | 0.038 | 0.037 | 0.036 | negative |
| 57222 153 | 0.038 | 0.036 | 0.041 | 0.037 | 0.036 | negative |
| 56746 226 | 0.038 | 0.036 | 0.038 | 0.036 | 0.034 | negative |
| F9-1278 | 0.037 | 0.024 | 0.038 | 0.036 | 0.034 | negative |
| 57238 | 0.037 | 0.035 | 0.037 | 0.036 | 0.035 | negative |
| 2873 | 0.037 | 0.034 | 0.036 | 0.033 | 0.034 | negative |
| 22151 80 | 0.036 | 0.026 | 0.039 | 0.036 | 0.047 | negative |
| 57611 216 | 0.036 | 0.035 | 0.067 | 0.043 | 0.044 | negative |
| 57211 147 | 0.036 | 0.035 | 0.039 | 0.037 | 0.034 | negative |
| F9-1211 | 0.035 | 0.033 | 0.036 | 0.035 | 0.031 | negative |
| mean | 0.041 | 0.035 | 0.042 | 0.037 | 0.036 | |
| std. deviation | 0.007 | 0.005 | 0.008 | 0.005 | 0.004 | |

Although various specific embodiments of the present invention have been described herein, it is to be understood that the invention is not limited to those precise embodiments and that various changes or modifications can be affected therein by one skilled in the art without departing from the scope and spirit of the invention.

What is claimed is:

1. A method for detecting infection of FIV in felids comprising:
   (a) obtaining a biological sample from a felid;
   (b) contacting the sample with an antigen consisting of SEQ ID NO:9, consisting of SEQ ID NO:20 or comprising an FIV Env peptide selected from the group consisting of SEQ ID NO:1-8 and 10 under conditions that permit antibody-antigen binding, wherein said antigen is attached to a solid phase;
   (c) detecting for antibody-antigen binding, wherein:
   (i) a positive result is indicative of an FIV-infected felid;
   (ii) a negative result is indicative of an uninfected felid.

2. A method for detecting vaccination and/or infection of FIV in felids comprising:
   (a) obtaining a first biological sample from a felid;
   (b) contacting the sample with a first antigen consisting of SEQ ID NO:9, consisting of SEQ ID NO:20 or comprising an FIV Env peptide selected from the group consisting of SEQ ID NO: 1-8 and 10 under conditions that permit antibody-antigen binding, wherein said first antigen is attached to a solid phase;
   (c) contacting the biological sample with a second antigen comprising an FIV Gag polypeptide, wherein the second antigen is attached to a solid phase under conditions that permit antibody-antigen binding,
   (d) detecting for antibody-antigen binding, wherein
   (i) a positive result in both step (b) and step (c) is indicative of an FIV-infected felid;
       (ii) a negative result in both step (b) and step (c) is indicative of an unvaccinated and uninfected feud;
       (iii) a negative result in step (c) and a positive result in step (b) is indicative of an uninfected feud that has been vaccinated with the a whole-killed FIV vaccine that comprises an inactivated FIV Env protein.

3. The method of claim 2 further comprising obtaining a second biological sample from the felid detected positive in step (d)(i) at about 10 to 12 weeks after the first biological sample is taken, and repeating step (b), wherein a positive result for the second sample is confirmative of an FIV-infected felid, and a negative result for the second sample is indicative of an uninfected felid that has been vaccinated with the whole-killed FIV vaccine within about 12 weeks before obtaining the first sample.

4. The method of claim 2, wherein the FTV Gag polypeptide is FIV p15 or FIV p24.

5. The method of claim 1 wherein the first antigen consists of SEQ ID NO:9.

6. The method of claim 1 wherein the first antigen consists of SEQ ID NO:20.

7. The method of claim 1 wherein the first antigen comprises SEQ ID NO:1.

8. The method of claim 1 wherein the first antigen comprises SEQ ID NO:2.

9. The method of claim 1 wherein the first antigen comprises SEQ ID NO:3.

10. The method of claim 1 wherein the first antigen comprises SEQ ID NO:4.

11. The method of claim 1 wherein the first antigen comprises SEQ ID NO:5.

12. The method of claim 1 wherein the first antigen comprises SEQ ID NO:6.

13. The method of claim 1 wherein the first antigen comprises SEQ ID NO:7.

14. The method of claim 1 wherein the first antigen comprises SEQ ID NO:8.

15. The method of claim 1 wherein the first antigen comprises SEQ ID NO:10.

* * * * *

SEQUENCE LISTING

<160> NUMBER OF SEQ ID NOS: 20

<210> SEQ ID NO 1
<211> LENGTH: 45
<212> TYPE: PRT
<213> ORGANISM: Artificial sequence
<220> FEATURE:
<223> OTHER INFORMATION: Synthetic polypeptide

<400> SEQUENCE: 1

Glu Leu Gly Ser Asn Gln Asn Gln Phe Phe Ser Lys Val Pro Pro Glu
1               5                   10                  15

Leu Trp Lys Arg Tyr Asn Lys Ser Lys Ser Lys Ser Lys Ser Lys Asn
            20                  25                  30

Arg Trp Glu Trp Arg Pro Asp Phe Glu Ser Glu Lys Cys
        35                  40                  45

<210> SEQ ID NO 2
<211> LENGTH: 45
<212> TYPE: PRT
<213> ORGANISM: Artificial sequence
<220> FEATURE:
<223> OTHER INFORMATION: Synthetic polypeptide

<400> SEQUENCE: 2

Cys Asn Arg Trp Glu Trp Arg Pro Asp Phe Glu Ser Glu Lys Ser Lys
1               5                   10                  15

Ser Lys Ser Lys Ser Met Gln Glu Leu Gly Ser Asn Gln Asn Gln Phe
            20                  25                  30

Phe Ser Lys Val Pro Pro Glu Leu Trp Lys Arg Tyr Asn
        35                  40                  45

<210> SEQ ID NO 3
<211> LENGTH: 46
<212> TYPE: PRT
<213> ORGANISM: Artificial sequence
<220> FEATURE:
<223> OTHER INFORMATION: Synthetic polypeptide

<400> SEQUENCE: 3

Cys Trp Glu Trp Arg Pro Asp Phe Glu Ser Arg Glu Leu Gly Ser
1               5                   10                  15

Asn Gln Asn Gln Phe Phe Ser Lys Ser Phe Phe Gln Asn Gln Asn Ser
            20                  25                  30

Gly Leu Glu Leu Gly Ser Asn Gln Asn Gln Phe Phe Ser Lys
        35                  40                  45

<210> SEQ ID NO 4
<211> LENGTH: 42
<212> TYPE: PRT
<213> ORGANISM: Artificial sequence
<220> FEATURE:
<223> OTHER INFORMATION: Synthetic polypeptide

<400> SEQUENCE: 4

Cys Asn Arg Trp Asp Trp Arg Pro Asp Phe Glu Ser Lys Lys Ser Lys
1               5                   10                  15

Thr Ala Phe Ala Met Gln Glu Leu Gly Ser Asn Gln Asn Gln Phe Phe
            20                  25                  30

Ser Lys Ile Pro Leu Glu Leu Trp Thr Arg
        35                  40

```
<210> SEQ ID NO 5
<211> LENGTH: 38
<212> TYPE: PRT
<213> ORGANISM: Artificial sequence
<220> FEATURE:
<223> OTHER INFORMATION: Synthetic polypeptide

<400> SEQUENCE: 5

Cys Asn Arg Trp Glu Trp Arg Pro Asp Phe Glu Ser Glu Lys Met Gln
1               5                   10                  15

Glu Leu Gly Ser Asn Gln Asn Gln Phe Phe Ser Lys Val Pro Pro Glu
            20                  25                  30

Leu Trp Lys Arg Tyr Asn
        35

<210> SEQ ID NO 6
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 6

Thr Ala Phe Ala Met Gln Glu Leu Gly Ser Asn Gln Asn Gln Phe Phe
1               5                   10                  15

Ser Lys

<210> SEQ ID NO 7
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 7

Thr Ala Phe Ala Met Gln Glu Leu Gly Cys Asn Gln Gln Gln Phe Phe
1               5                   10                  15

Cys Ala

<210> SEQ ID NO 8
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 8

Tyr Thr Ala Phe Ala Met Gln Glu Ile Gly Cys Asn Gln Asn Gln Phe
1               5                   10                  15

Phe Cys Ala

<210> SEQ ID NO 9
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 9

Glu Leu Gly Cys Asn Gln Asn Gln Phe Phe Cys Lys
1               5                   10
```

```
<210> SEQ ID NO 10
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 10

Cys Glu Gly Ser Asn Gln Asn Gln Phe Phe Ser Lys
1               5                   10

<210> SEQ ID NO 11
<211> LENGTH: 22
<212> TYPE: PRT
<213> ORGANISM: Artificial sequence
<220> FEATURE:
<223> OTHER INFORMATION: Synthetic polypeptide

<400> SEQUENCE: 11

Glu Leu Gly Ser Asn Gln Asn Gln Phe Phe Ser Lys Val Pro Pro Glu
1               5                   10                  15

Leu Trp Lys Arg Tyr Asn
            20

<210> SEQ ID NO 12
<211> LENGTH: 22
<212> TYPE: PRT
<213> ORGANISM: Artificial sequence
<220> FEATURE:
<223> OTHER INFORMATION: Synthetic polypeptide

<400> SEQUENCE: 12

Met Gln Glu Leu Gly Ser Asn Gln Asn Gln Phe Phe Ser Pro Pro Glu
1               5                   10                  15

Leu Trp Lys Arg Tyr Asn
            20

<210> SEQ ID NO 13
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 13

Glu Leu Gly Ser Asn Gln Asn Gln Phe Phe Ser Lys
1               5                   10

<210> SEQ ID NO 14
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 14

Leu Gly Ser Asn Gln Asn Gln Phe Phe Ser
1               5                   10

<210> SEQ ID NO 15
<211> LENGTH: 26
<212> TYPE: PRT
<213> ORGANISM: Artificial sequence
<220> FEATURE:
<223> OTHER INFORMATION: Synthetic polypeptide

<400> SEQUENCE: 15
```

```
Thr Ala Phe Ala Met Gln Glu Leu Gly Ser Asn Gln Asn Gln Phe Phe
1               5                   10                  15

Ser Lys Ile Pro Leu Glu Leu Trp Thr Arg
            20                  25
```

<210> SEQ ID NO 16
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 16

```
Asn Arg Trp Glu Trp Arg Pro Asp Phe Glu Ser Glu Lys Cys
1               5                   10
```

<210> SEQ ID NO 17
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 17

```
Cys Asn Arg Trp Glu Trp Arg Pro Asp Phe Glu Ser Glu Lys
1               5                   10
```

<210> SEQ ID NO 18
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 18

```
Cys Trp Glu Trp Arg Pro Asp Phe Glu Ser Glu Arg
1               5                   10
```

<210> SEQ ID NO 19
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 19

```
Cys Asn Arg Trp Asp Trp Arg Pro Asp Phe Glu Ser Lys Lys
1               5                   10
```

<210> SEQ ID NO 20
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 20

```
Cys Glu Leu Gly Cys Asn Gln Asn Gln Phe Phe Cys Lys
1               5                   10
```